(12) United States Patent
Marino et al.

(10) Patent No.: US 6,221,082 B1
(45) Date of Patent: Apr. 24, 2001

(54) SPINAL SURGERY GUIDANCE PLATFORM

(75) Inventors: James F. Marino, La Jolla; Corbett W. Stone, San Diego; Dan K. Ahlgren, San Diego; Troy K. Christopher, San Diego; James T. McKinley, Woodside, all of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/326,739

(22) Filed: Jun. 4, 1999

Related U.S. Application Data (60) Provisional application No. 60/088,663, filed on Jun. 9, 1998, provisional application No. 60/120,663, filed on Feb. 12, 1999, and provisional application No. 60/129,703, filed on Apr. 16, 1999.

(51) Int. Cl.⁷ .................................................. A61B 19/00
(52) U.S. Cl. ........................................................ 606/130
(58) Field of Search ........................... 606/54, 53, 56, 606/96, 97, 98, 130; 604/116

(56) References Cited

U.S. PATENT DOCUMENTS

| | | |
|---|---|---|
| 1,747,788 | 2/1930 | Straus . |
| 2,666,430 * | 1/1954 | Gispert .................................. 606/96 |
| 4,254,763 | 3/1981 | McCready et al. . |
| 4,350,159 | 9/1982 | Gouda . |
| 4,457,300 | 7/1984 | Budde . |
| 4,638,798 | 1/1987 | Shelden et al. . |
| 4,638,799 | 1/1987 | Moore . |
| 4,653,509 * | 3/1987 | Oloff et al. ........................... 606/130 |
| 4,672,957 * | 6/1987 | Hourahane .............................. 606/96 |
| 4,722,336 | 2/1988 | Kim et al. . |
| 4,723,544 * | 2/1988 | Moore et al. ......................... 606/130 |
| 4,805,599 | 2/1989 | Ray . |
| 4,841,967 | 6/1989 | Chang et al. . |
| 4,926,849 | 5/1990 | Downey . |
| 4,953,540 | 9/1990 | Ray et al. . |
| 4,969,888 | 11/1990 | Scholten et al. . |
| 5,078,140 | 1/1992 | Kwoh . |
| 5,080,662 * | 1/1992 | Paul ...................................... 606/130 |
| 5,108,404 | 4/1992 | Scholten et al. . |
| 5,280,427 | 1/1994 | Magnusson et al. . |
| 5,284,130 | 2/1994 | Ratliff . |
| 5,308,352 * | 5/1994 | Koutrouvelis ........................ 604/116 |
| 5,397,323 | 3/1995 | Taylor et al. . |
| 5,454,810 * | 10/1995 | Pohl et al. .............................. 606/54 |
| 5,472,427 * | 12/1995 | Rammler ............................... 604/164 |
| 5,528,651 | 6/1996 | Leksell et al. . |
| 5,598,269 * | 1/1997 | Kitaevich et al. .................... 606/130 |
| 5,665,095 | 9/1997 | Jacobson . |
| 5,693,030 | 12/1997 | Lee et al. . |
| 5,769,820 | 6/1998 | Rammler . |
| 5,805,661 | 9/1998 | Leksell et al. . |
| 5,853,366 | 12/1998 | Dowlatshahi . |

* cited by examiner

*Primary Examiner*—Gene Mancene
*Assistant Examiner*—Eduardo C. Robert
(74) *Attorney, Agent, or Firm*—Townsend and Townsend and Crew LLP (57) ABSTRACT

A spinal surgery system having a base, a cross member suspended from the base, and a pair of cannula guides suspended from the cross member, wherein the cannula guides are adapted to hold cannulae received therein such that the canulae remain co-planar with one another as the cannula guides are moved to various positions in the patient's intervertebral plane. By first suspending a pair of radiopaque markers in the cannual guides, and then viewing the image of the radiopaque markers, the cannulae guides can be aligned so that when the radiopaque markers have been removed and replaced with cannulae, the cannulae can be positioned along various paths which are disposed in the patient's intervertebral plane such that surgical tools can be advanced in preferred paths toward the patient's intervertebral space.

21 Claims, 15 Drawing Sheets

SPINAL SURGERY GUIDANCE PLATFORM

CROSS-REFERENCES TO RELATED APPLICATIONS

The present application is a regular application claiming benefit under 35 USC §119(e) from U.S. Provisional Patent Application Serial No. 60/088,663 filed Jun. 9, 1998; U.S. Provisional Patent Application Serial No. 60/120,663 filed Feb. 12, 1999; and Provisional U.S. Patent Application Serial No. 60/129,703 filed Apr. 16, 1999. Each of these applications is incorporated herein by reference in its entirety for all purposes.

TECHNICAL FIELD

The present invention relates to surgical guidance systems.

BACKGROUND OF THE INVENTION

When performing minimally invasive percutaneous spinal surgery on a prone lying patient, such as when accessing the patient's intervertebral area for the insertion of intervertebral inserts or the performing of a discectomy, the various necessary surgical tools and/or inserts should preferably access the patient's spine in a posterolateral approach which is co-planar to the intervertebral plane passing between two selected adjacent vertebrae. Maintaining accurate positioning and guidance of surgical tools in this intervertebral plane has proven quite difficult to achieve in practice. Such positioning difficulties are further complicated by the fact that the intervertebral plane passing between any two adjacent vertebrae will be unique to that pair of adjacent vertebrae due to natural lordotic spinal curvature, sagittal plane variances as well as coronal plane variances.

SUMMARY OF THE INVENTION

The present invention provides a guidance platform for positioning one or more surgical instruments in an intervertebral plane which passes between two adjacent vertebrae in the patient's spine such that the surgical instrument(s) can be held at a preferred angle while advanced in a percutaneous cannulated approach towards the patient's intervertebral space.

An advantage of the present invention is that it can be used to support operating cannulae in the preferred intervertebral plane passing between any two selected vertebrae such that various surgical instruments and/or intervertebral inserts can be passed through the cannulae and into the patient's intervertebral space in a preferred posterolateral approach.

Preferably, the present invention is used to position two cannulae, with each approaching the patient's intervertebral space posterolaterally from the same or opposite sides. However, the positioning of only one cannula co-planar with the selected intervertebral plane is also contemplated. When separately positioning two operating cannulae, another advantage of the present invention is that it enables the simultaneous positioning of first and second surgical instruments with respect to one another and with respect to the patient's spine such that each surgical instrument can be advanced into the patient from opposite posterolateral angles of approach.

DESCRIPTION OF THE PREFERRED EMBODIMENT

The present invention comprises a spinal surgery guidance platform and a preferred method of operating a spinal surgery guidance platform. Accordingly, the apparatus of the present invention will be described in conjunction with a preferred description of its manner of use below.

Figure 1A:
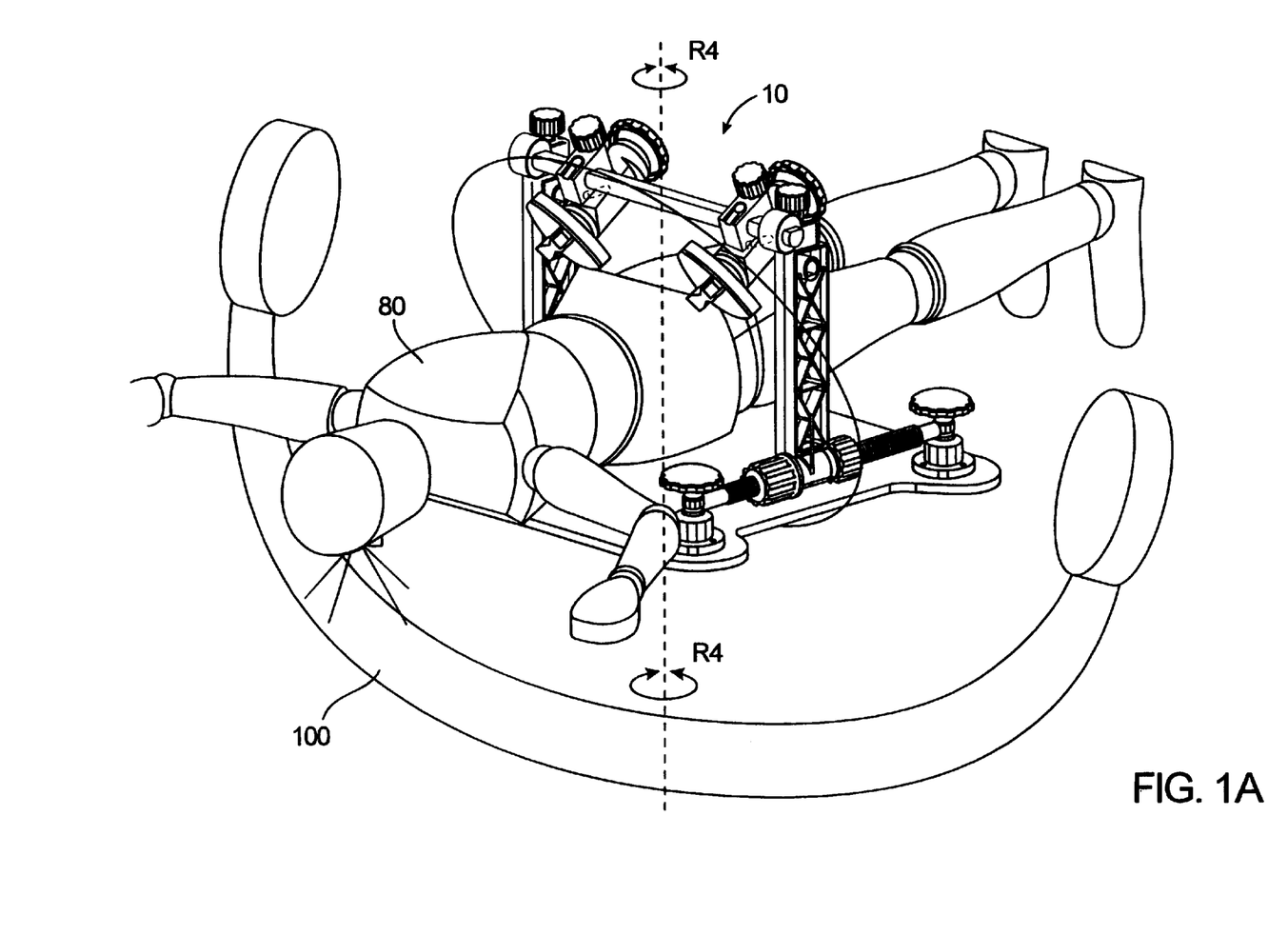
FIG. 1A is a view of a prone-lying patient positioned under the present guidance platform with an image intensifier taking a lateral image through the patient.
Figure 1B:
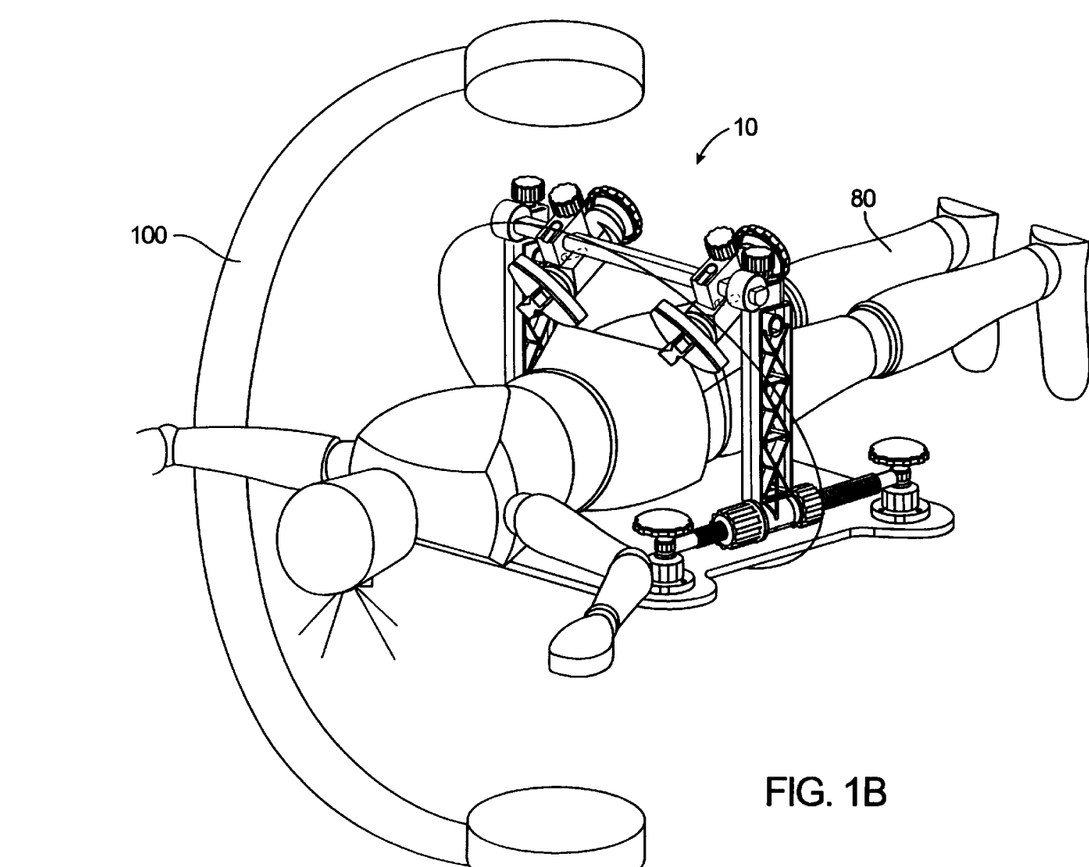
FIG. 1B is a view of a prone-lying patient positioned under the present guidance platform with an image intensifier taking an anterior-posterior image through the patient.
Figure 2:
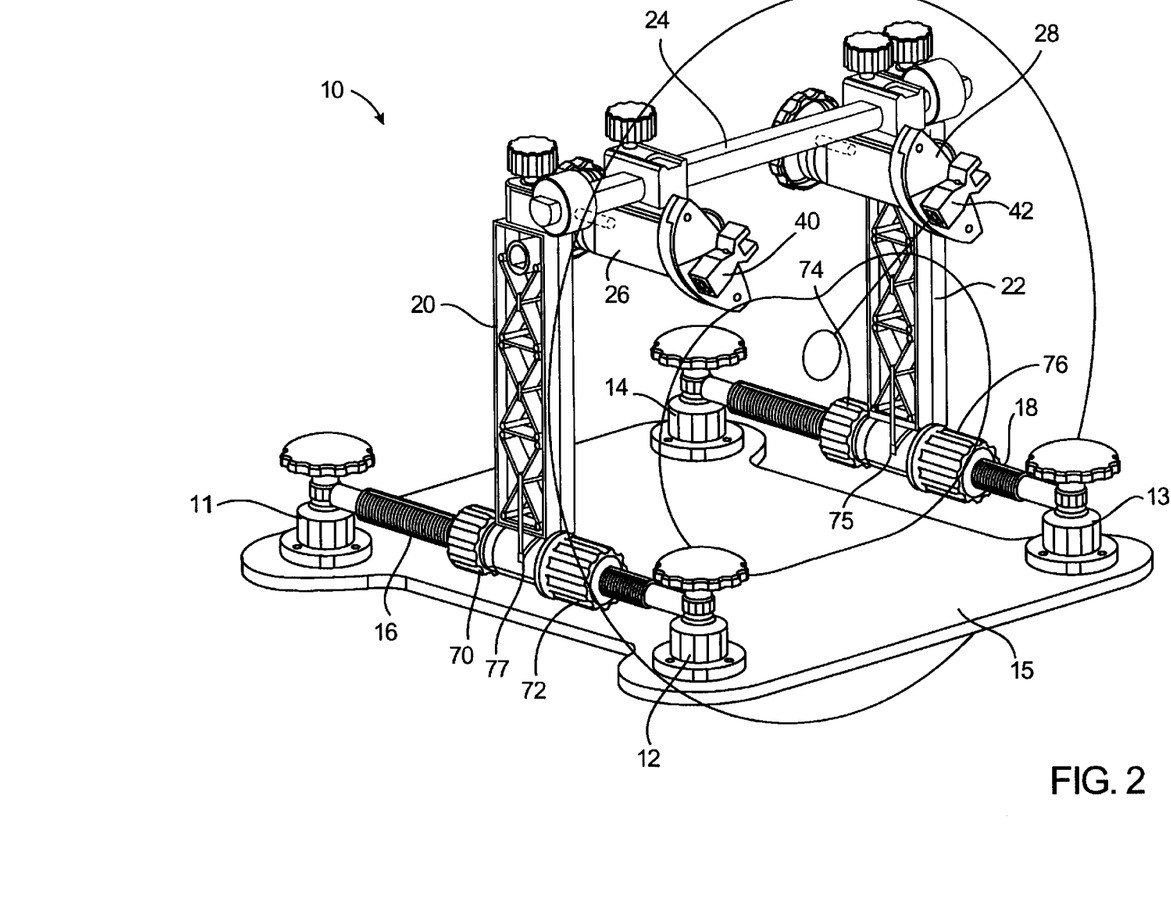
FIG. 2 is a perspective view of the present guidance platform showing system components.

As is seen in FIGS. 1A and 1B, a guidance platform 10 is first positioned over the back of a prone-lying patient 80 as shown. As shown in FIG. 1A, a radio image intensifier 100 can be positioned to take lateral image through patient 80; and as shown in FIG. 1B, image intensifier 100 can also be rotated to take oblique or anterior-posterior radio-image through patient 80.

As is seen in FIGS. 2 to 6, guidance platform 10 preferably comprises a base which may have four support posts 11, 12, 13, and 14 which are adapted to be connected to a radio translucent surgical table 15. Guide rails 16 and 18 span between support posts 11 to 12 and 13 to 14 respectively. Upwardly extending support members 20 and 22 are connected to guide rails 16 and 18 such that they can be individually moved back and forth in direction D1 along guide rails 16 and 18 to preferred positions as will be explained.

Figure 13:
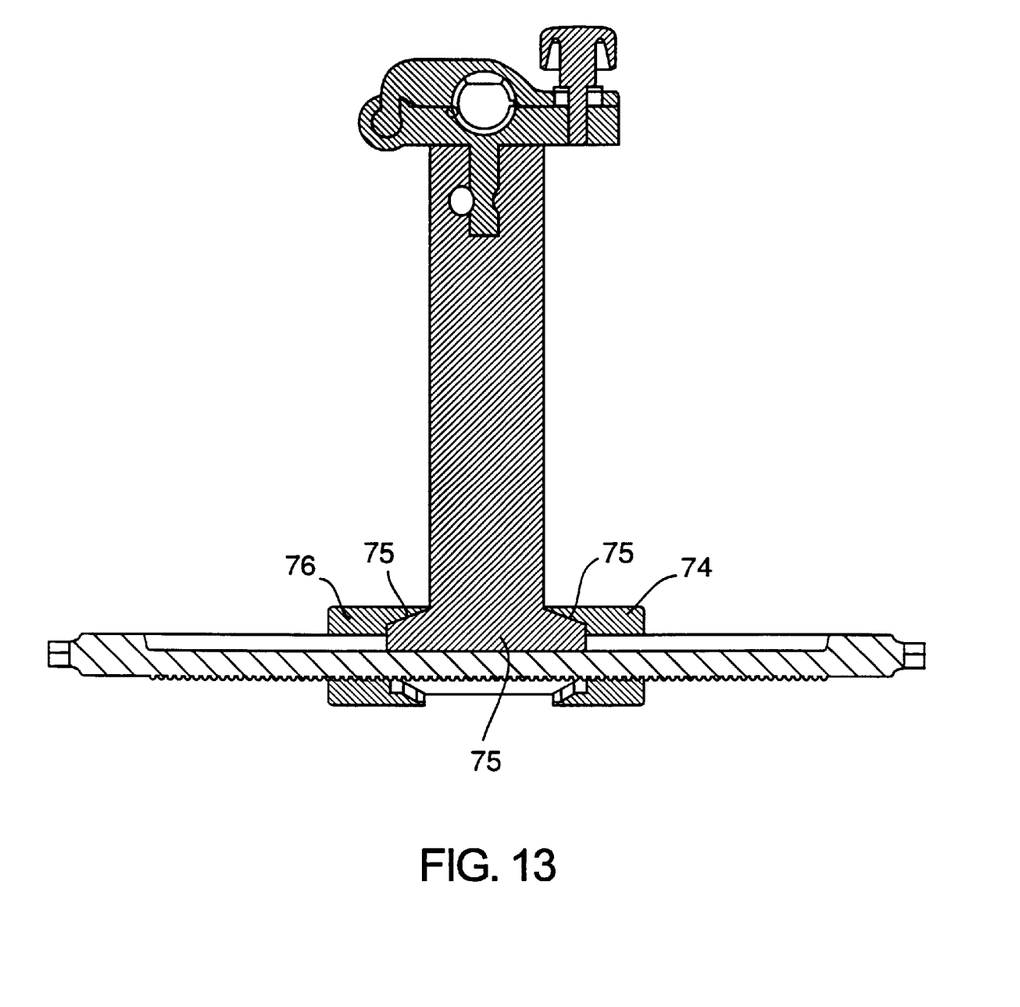
FIG. 13 is a sectional elevation view of the mechanism connecting an upward support to a guide rail.

Preferably, upwardly extending support members 20 and 22 are adapted to individually be positionable along guide rails 16 and 18 with tightening fasteners 70, 72, 74 and 76 being threaded for movement along guide rails 16 and 18. Fasteners 70, 72, 74 and 76 preferably are threaded to pass over the ends of support bases 75 and 77, as can be seen best in FIG. 13. By tightening fasteners 70, 72, 74 and 76 against support bases 75 and 77, supports 20 and 22 can be held in a locked position at preferred locations along guide rails 16 and 18, as desired. In addition, tightening fasteners 70, 72, 74 and 76 can be retracted from opposite ends of support base 75 such that support 20 can be easily lifted directly off of guide rails 16 and 18. As such, guidance platform 10 can be removed from guide rails 16 and 18 in an emergency, or as otherwise required. Preferably, guide rails 16 and 18 and tightening fasteners 70, 72, 74 and 76 are threaded for accurate positioning of supports 20 and 22.

A cross-member 24, which may preferably be horizontal, is positioned to span over the back of the patient between support members 20 and 22 as shown. A pair of cannula guide holders 26 and 28 are mounted to cross-member 24 as shown. Cannula guide holders 26 and 28 are adapted to rotate about a central longitudinal axis 30 of cross-member 24 in direction R1. Cannula guide holders 26 and 28 are also adapted to rotate about axes 32 and 34 respectively in directions R2.

Cannula guide holders 26 and 28 support cannula guides 40 and 42 which are mounted thereon as shown. Cannula guides 40 and 42 are used to support cannulae through which various surgical instruments are passed therethough. By positioning cannula guides 40 and 42 in a preferred intervertebral plane, operating cannulae and the various surgical instruments which are passed therethrough are also positioned in the selected intervertebral plane. As will also be explained, cannula guides 40 and 42 can be rotated within the intervertebral plane such that the various surgical instruments can be advanced into the patient's intervertebral space at preferred angles while remaining within the selected intervertebral plane.

After patient 80 has been placed in a prone-lying position, cannula guides 40 and 42 are then aligned with a preferred intervertebral plane 50, (seen in FIG. 6), by first aligning a pair of radio-opaque markers (41 and 43) suspended within the cannula guides with intervertebral plane 50, as follows.

Figure 4:
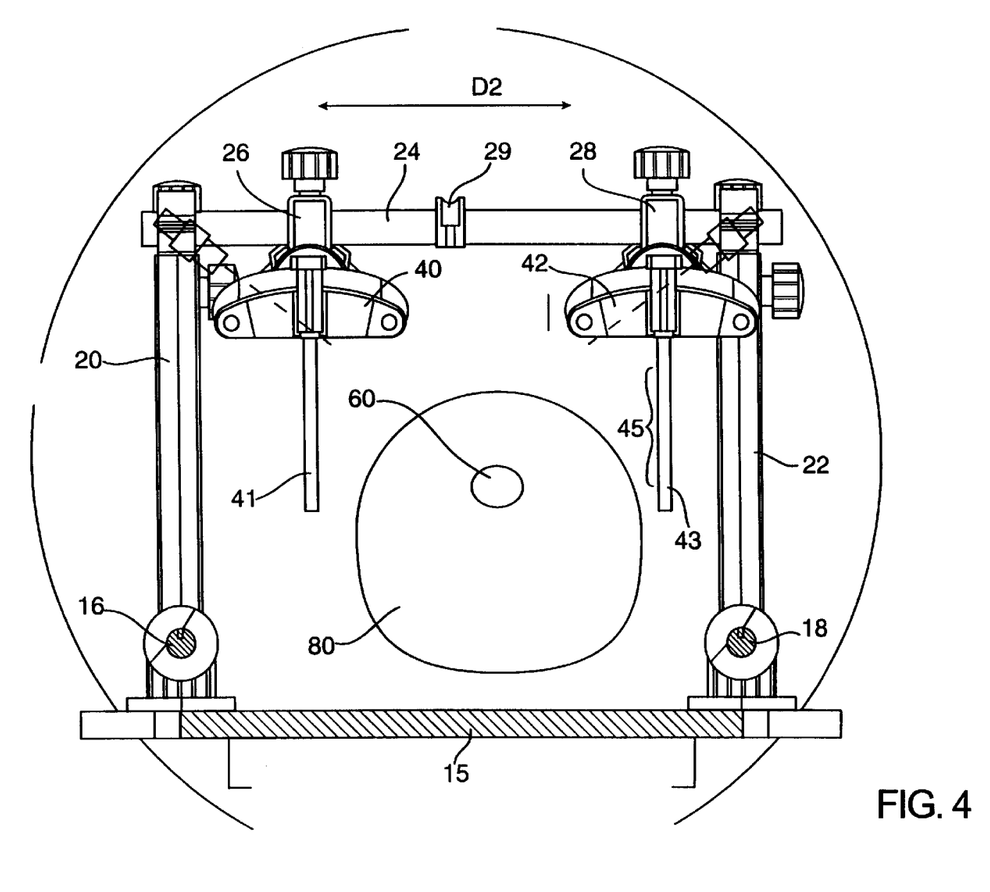
FIG. 4 is a rear elevation view of the present guidance platform.
Figure 5:
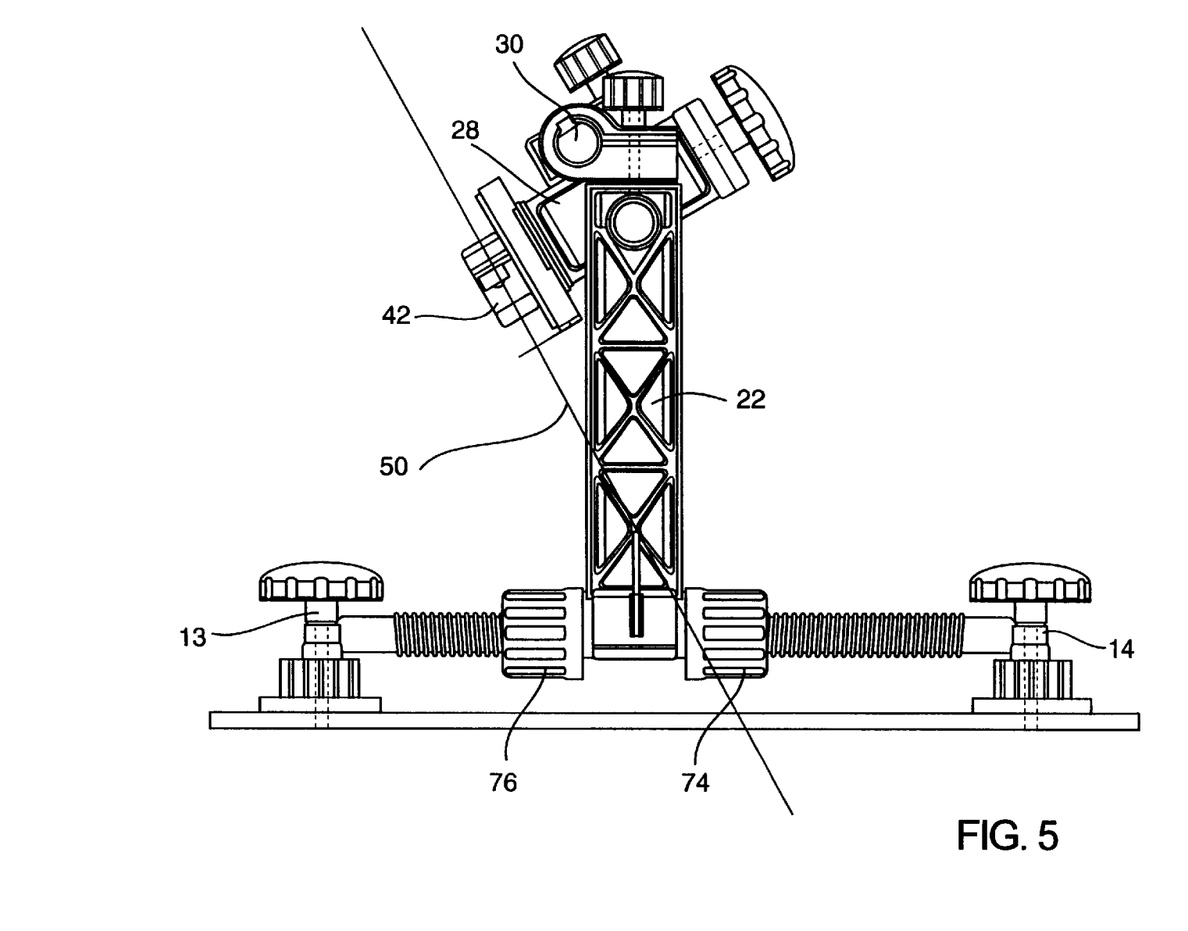
FIG. 5 is a lateral side elevation view of the present guidance platform.
Figure 6:
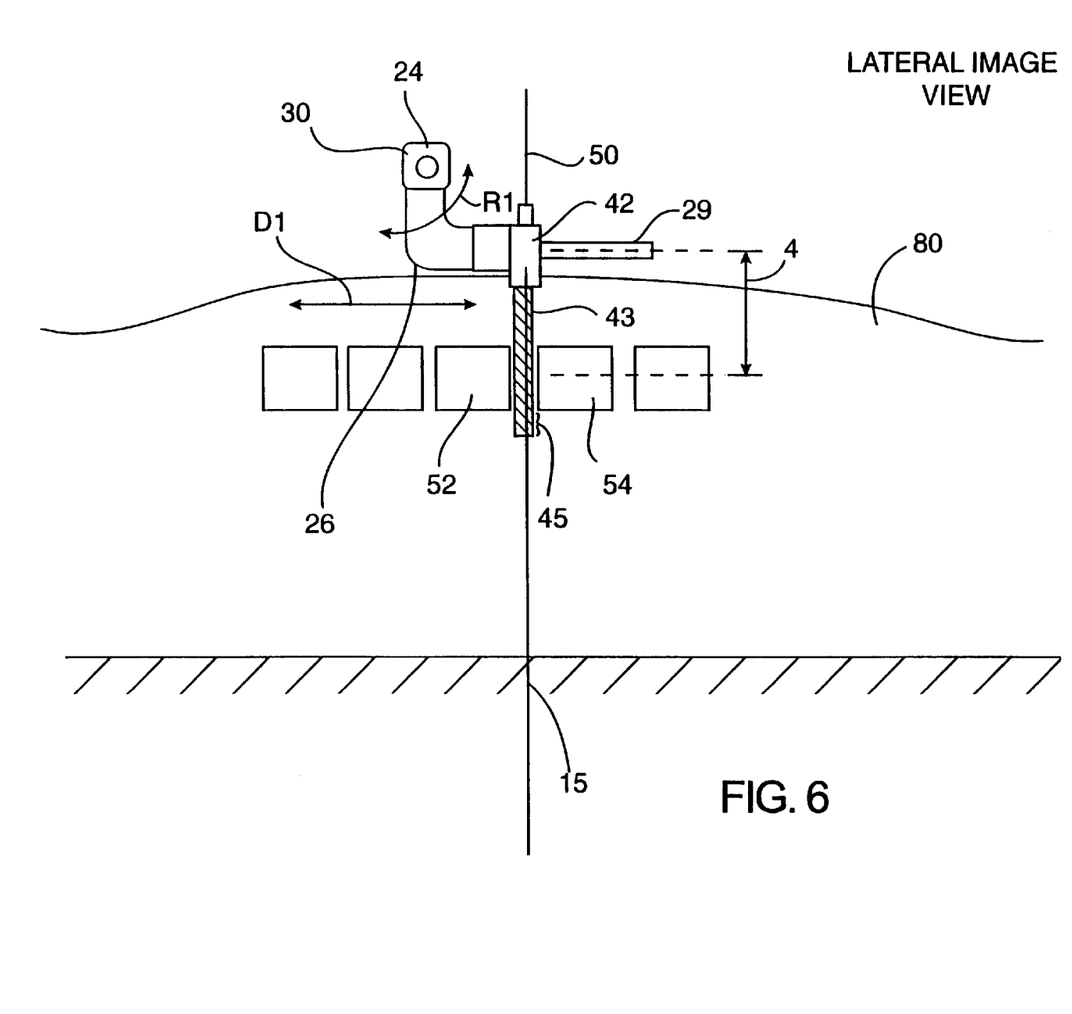
FIG. 6 is schematic representation of a lateral image view through the patient taken by the image intensifier of FIG. 1A with a first cannula guide aligned to hold a first radiopaque marker co-planar with a selected intervertebral plane.

As seen in FIG. 4, cannula guides 40 and 42 are each adapted to hold respective radiopaque markers 41 and 43 which are suspended therein as shown. Being radiopaque, the image of markers 41 and 43 will appear on a radio-image of the patient's vertebrae as generated by image intensifier 100. FIGS. 6 shows a lateral image view through the patient corresponding to FIG. 4 generated by image intensifier 100 positioned as shown in FIG. 1A to take such a lateral view through the patient.

Each of cannula guide holders 40 and 42 can separately be aligned with intervertebral plane 50 by separately aligning each of radiopaque markers 41 and 43 with intervertebral plane 50. For example, as can be seen in FIG. 6, cannula guide 42 can be aligned with intervertebral plane 50 passing between two selected vertebrae 50 and 52 by rotating cannula guide holder 28 in direction R1 and by separately moving support members 21 and 22 in direction D1 to locations such that an image of radiopaque marker 43 (suspended in cannula guide 42), is aligned with intervertebral plane 50, as shown.

Preferably, supports 20 and 22 are each moved independently of one another along guide rails 16 and 18 in direction D1, respectively. In addition, cannula guide holders 26 and 28 can be rotated in direction R1 independently of one another.

Accordingly, when viewing a lateral image through the patient, cannula guide 40 can then be aligned with intervertebral plane 50 passing between two selected vertebrae 50 and 52 by rotating cannula guide holder 26 in direction R1 and by moving support members 20 and 22 in direction D1 such that an image of radiopaque marker 41 (suspended in cannula guide 40), is aligned with intervertebral plane 50.

Figure 3:
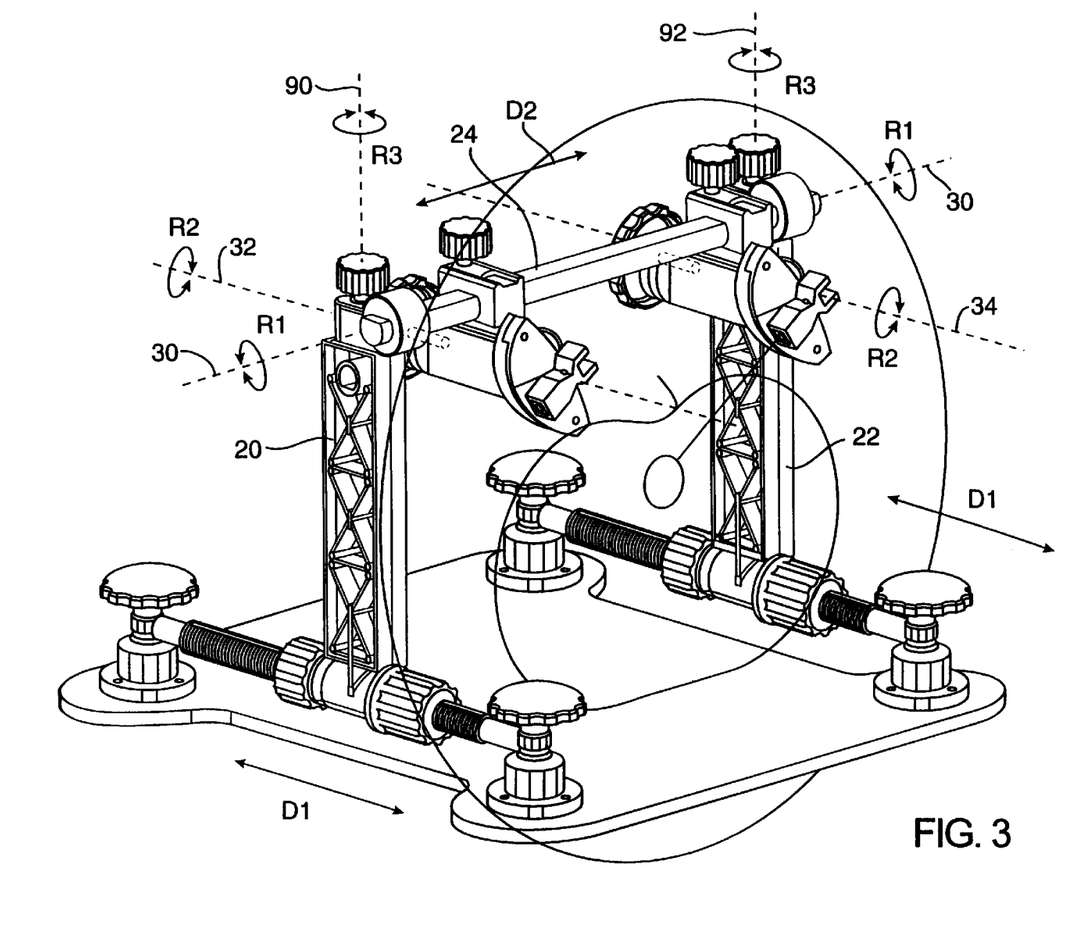
FIG. 3 is a perspective view of the present guidance platform showing directions and angles of movement of various system components.

Due to each of supports 20 and 22 being separately movable along guide rails 16 and 18, the ends of cross member 24 are preferably adapted to rotate in directions R3 about axes 90 and 92 extending central through supports 20 and 22, as shown in FIG. 3. Accordingly, when taking the lateral image of FIG. 8, image intensifier 100 may be moved through various angles in direction R4 in FIG. 1A, to account for coronal variances of the positioning of the intervertebral plane.

In one optional aspect of the invention, cannula guide holders 26 and 28 are secured to cross-member 24 such that they remain co-planar with one another and rotate in unison in direction R1. In this optional aspect, cannula guide holders 26 and 28 can be aligned with intervertebral plane 50 together by positioning supports 20 and 22 at appropriate locations along guide rails 16 and 18, and rotating cannula guide holders 26 and 28 together in direction R1 about axis 30, while viewing a lateral radio-image through patient 80.

Alternatively, cannula guide holders 26 and 28 can instead be separately rotatable in direction R1 around axis 30, facilitating separate alignment of each of markers 41 and 43 with intervertebral plane 50 by appropriate rotational and translational movement of guide holders 26 and 28 in directions R1 and D1, respectively.

In a preferred aspect, marker 41 will have radiopaque beads therein and radiopaque marker 43 will have a series of radiopaque parallel lines printed thereon, (or vice versa). Cannulae guide holders 26 and 28 can then be aligned by superimposing the image of the radiopaque beads on one marker within the series of radiopaque parallel indicia lines on the other marker. Other suitable radio-viewable indicia on radiopaque markers 41 and 43 can also be used.

Figure 14:
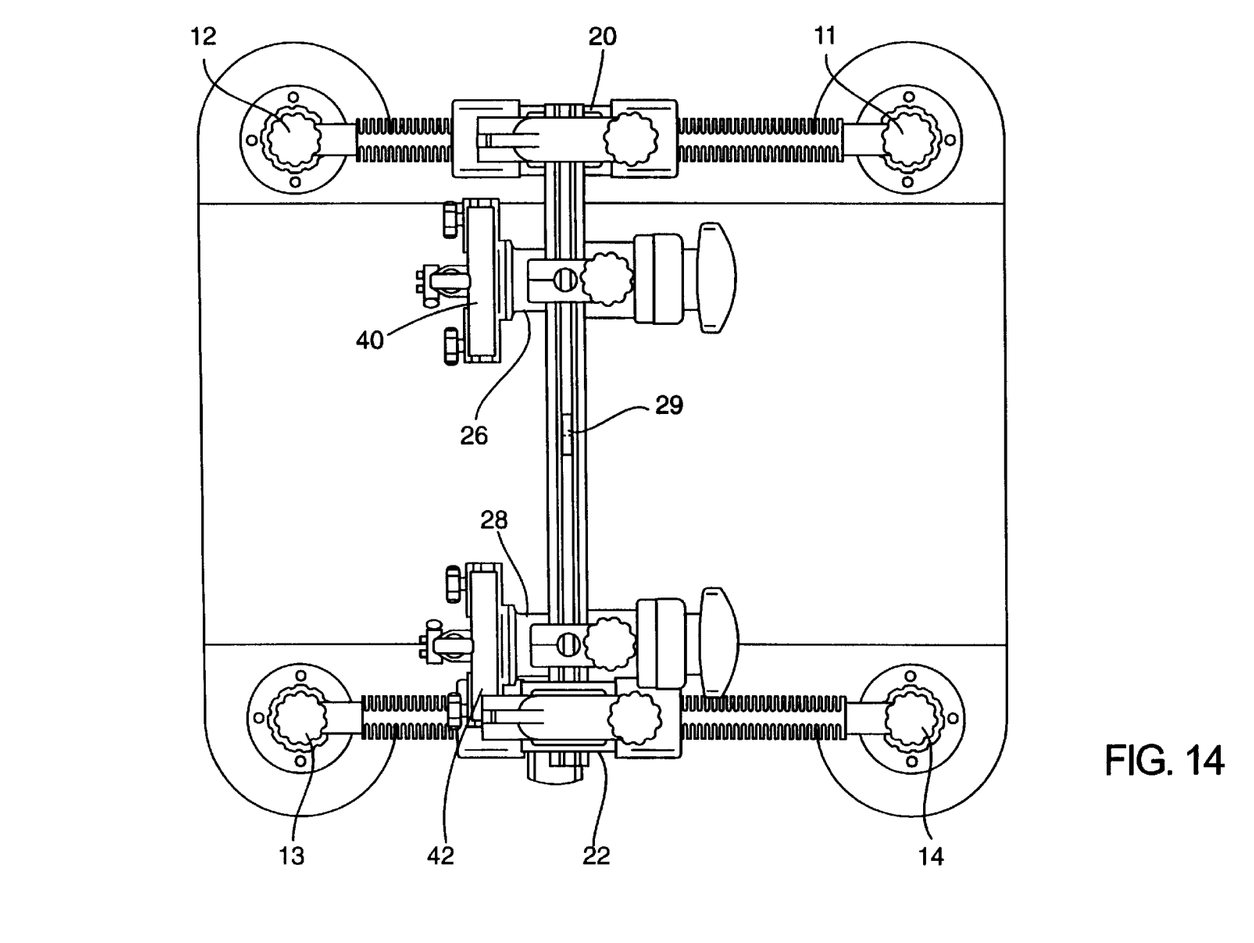
FIG. 14 is a top plan view of the present guideframe.

When aligning markers 41 or 43 to be co-planar with intervertebral plane 50, markers 41 and 43 will preferably initially be suspended to hang vertically downward beside prone-lying patient 80 as is shown for markers 41 and 43 in FIG. 4. Marker 43 preferably has depth indicia 45 (FIG. 14) printed thereon which are viewable in the radio-image. Accordingly, when using image intensifier 100 to view the lateral view through the patient's spine as shown in FIG. 6, a depth 4 between cross member 24, (or horizontal radio-opaque marker 29), and the patient's intervertebral space 60 can be easily measured on indicia 45.

After markers 41 and 43 have been aligned with intervertebral plane 50, cannula guides 26 and 28 are then secured from translating in direction D1 and rotating in direction R1, such that cannula guide holders 40 and 42 also remain free to rotate to positions within intervertebral plane 50.

Figure 7:
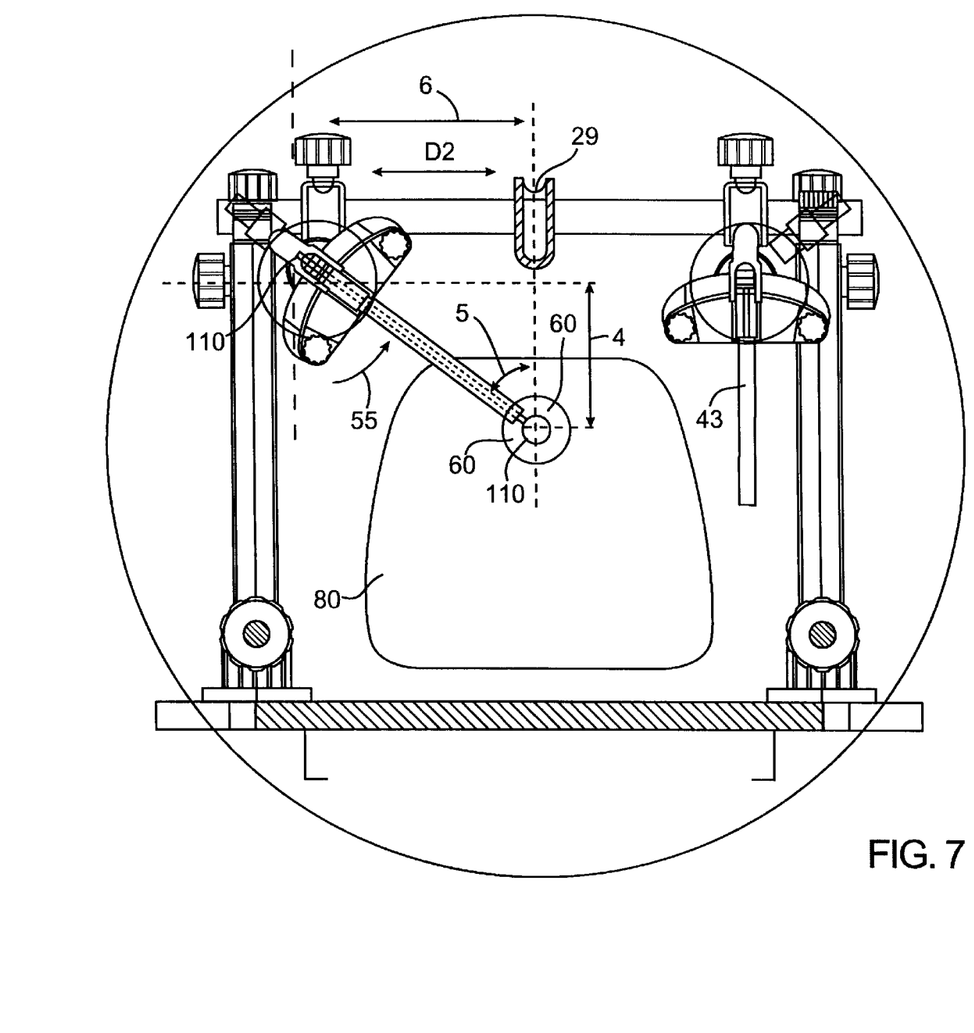
FIG. 7 is a rear elevation view showing a first operating cannula accessing the patient's intervertebral area in a posterolateral approach.

Subsequent to the alignment of cannula guides 40 and 42 with intervertebral plane 50, the cannula guide holders 26 and 28 can each be rotated about axes 32 and 34 respectively so as to position various surgical instruments received therein in a various posterolateral approaches to the patient's spine, as follows. As is shown in FIG. 7, marker 41 is removed from cannula guide holder 40 and is replaced with a percutaneously introduced cannula 55. Cannula 55 can be used for inserting any number of different surgical instruments 110 therethrough and into intervertebral space 60 in a preferred posterolateral angle 5 as shown. Preferred surgical instruments may comprise intervertebral inserts, bone decorticators, cameras, articulating forceps, intervertebral insert positioning systems, bone-graft introducers, electrocoagulators, bone wax applicators, shavers and curettes.

Cannula guide 40 can be moved in direction D2 and rotated in direction R2 while still remaining in intervertebral plane 50. Accordingly, a desired angle of posterolateral approach, (angle 5), into the patient's intervertebral area 60 can be selected, while the path of cannula 55 and any surgical instrument advanced therethrough remains within intervertebral plane 50, as follows.

Preferred posterolateral angle of approach 5 can be determined by the surgeon reviewing pre-operative MRI's to determine a safe angle of approach. Vertical distance 4 can be determined as shown in FIG. 6, by viewing the position of the patient's vertebrae 52 and 54 relative to one or both or radiopaque markers 41 and 43 with the image intensifier positioned to take a lateral image. Knowing distance 4 and preferred angle 5, the surgeon may determine distance 6 by simple geometric tables. Accordingly, cannula guide 26 can then be moved along cross-member 24 in direction D2 to a distance 6 and cannula guide 26 can then be rotated by angle 7 such that cannula 55 can be introduced into intervertebral space 60 at preferred posterolateral angle 5. Preferably, the patient's spine is first viewed and centered under the mid-sagittal marker 29 with the image intensifier in the anterior-posterior projection as shown in FIG. 1B. Thereafter, cannula guides 26 and 28 can be positioned at distance 6 from the center of the patient's spine. In various aspects of the invention, mid-sagittal marker 29 can be moved along cross member 24 such that it can be positioned above the patient's spine. Preferably as well, indicia along the length of cross member 24 assists in positioning the cannula guides 26 and 28 therealong. Most preferably, the indicia is attached to the mid-sagittal marker and moves along the cross member as the mid-sagittal marker is moved therealong.

As such, the operator can view the advancement of cannula 55 toward intervertebral space 60 in an anterior-posterior image. Similarly, positioning the image intensifier as shown in FIG. 1A, allows the operator to view the advancement of cannula 50 into intervertebral space 60 in a lateral image. As can be appreciated, further views of advancing cannula 55 can be taken by positioning image intensifier at positions between that shown in FIGS. 1A and 1B.

Figure 8:
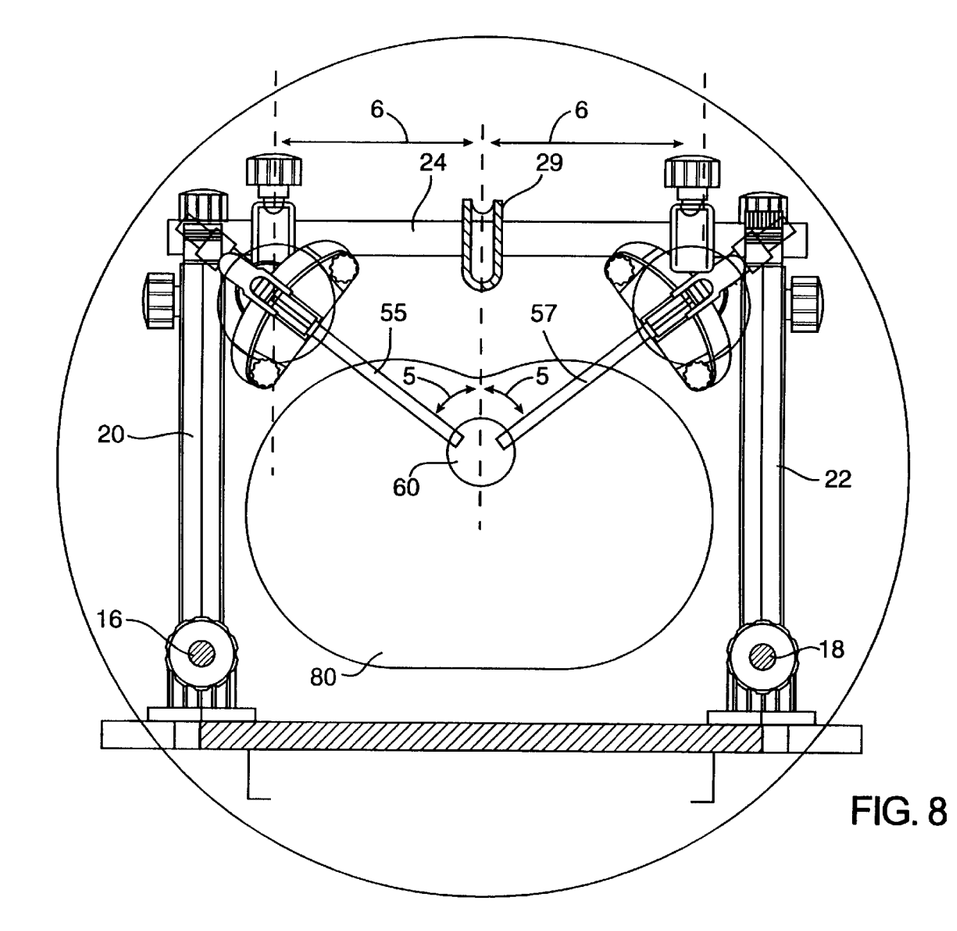
FIG. 8 is a rear elevation view showing a first and second cannulae accessing the patient's intervertebral area in opposite posterolateral approaches.

Subsequently, as shown in FIG. 8, radiopaque marker 43 can then be removed and cannula guide 28 can be rotated into a mirror image position of cannula guide 26 using the procedure set forth above if the operator desired to enter intervertebral space 60 from the same angle 5 on both sides. Accordingly, by positioning cannula guide 28 the same distance 6 from mid-sagittal marker 29, and rotating cannula guide 28 to the same angle of that of cannula guide 26, accurate positioning of a second cannula 57 having the same angle 5 to the patient's spinal column can be easily achieved. FIG. 8 shows preferred 35 to 45 degree posterolateral angles of approach 5 into the patient's intervertebral region. FIGS. 15 and 16 show various expandable-end nerve displacement and race-track cross sectional shaped cannulae which may be supported in cannula guides 40 and 42.

Figure 9:
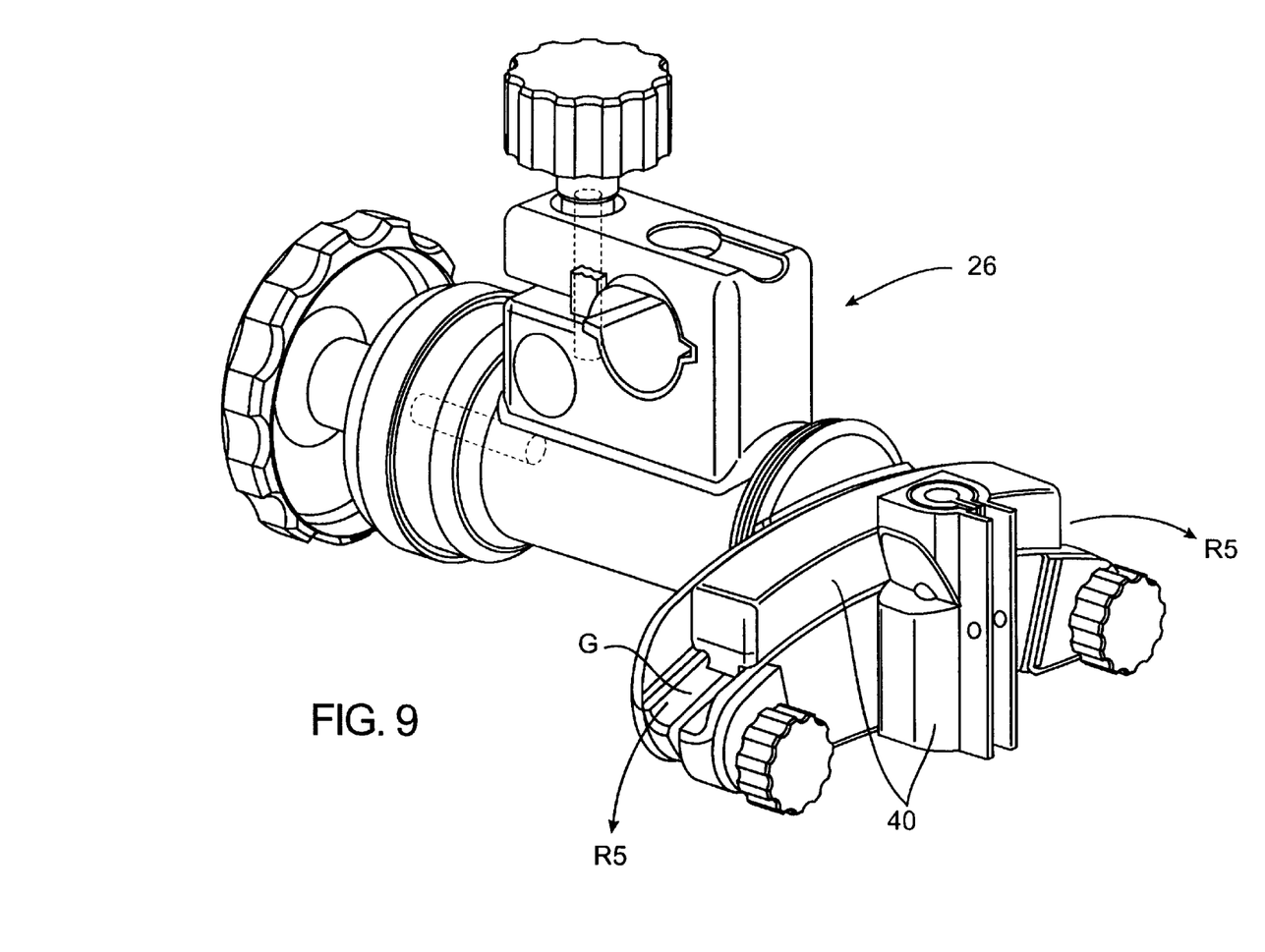
FIG. 9 shows further structural details of a cannula guide holder and attached mounting system.
Figure 11:
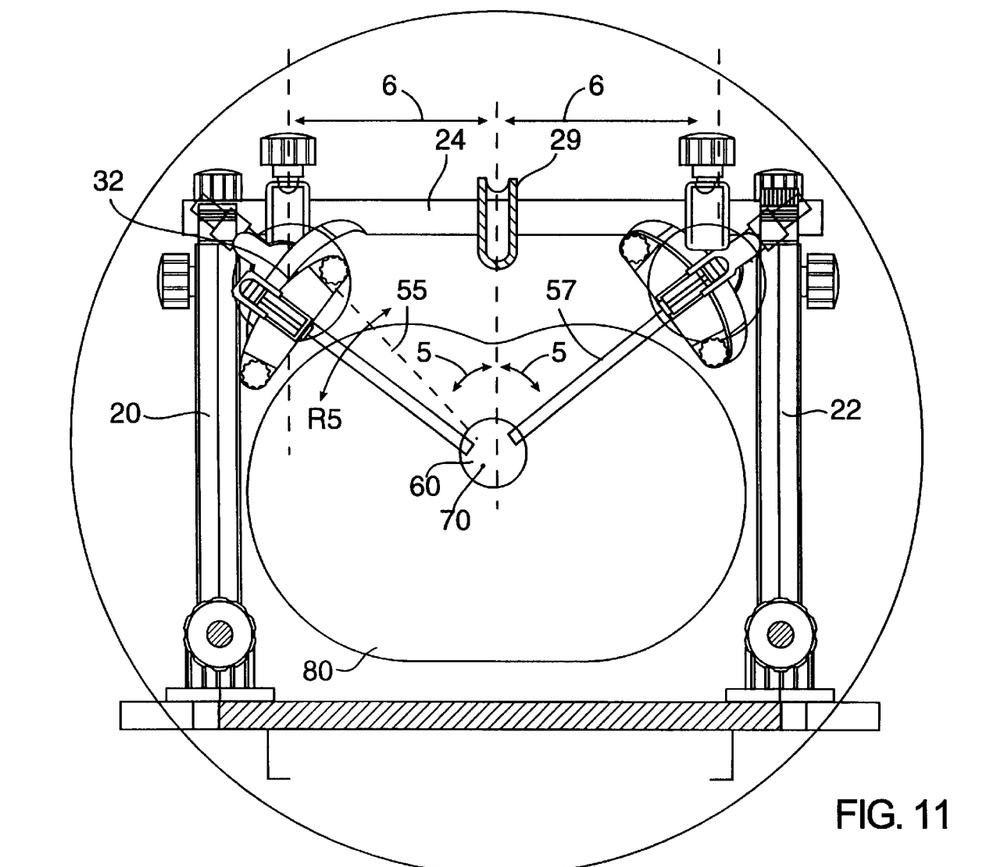
FIG. 11 shows a rear elevation view of a cannula guide adapted to rotate a cannula about a point at or near its distal end.
Figure 12:
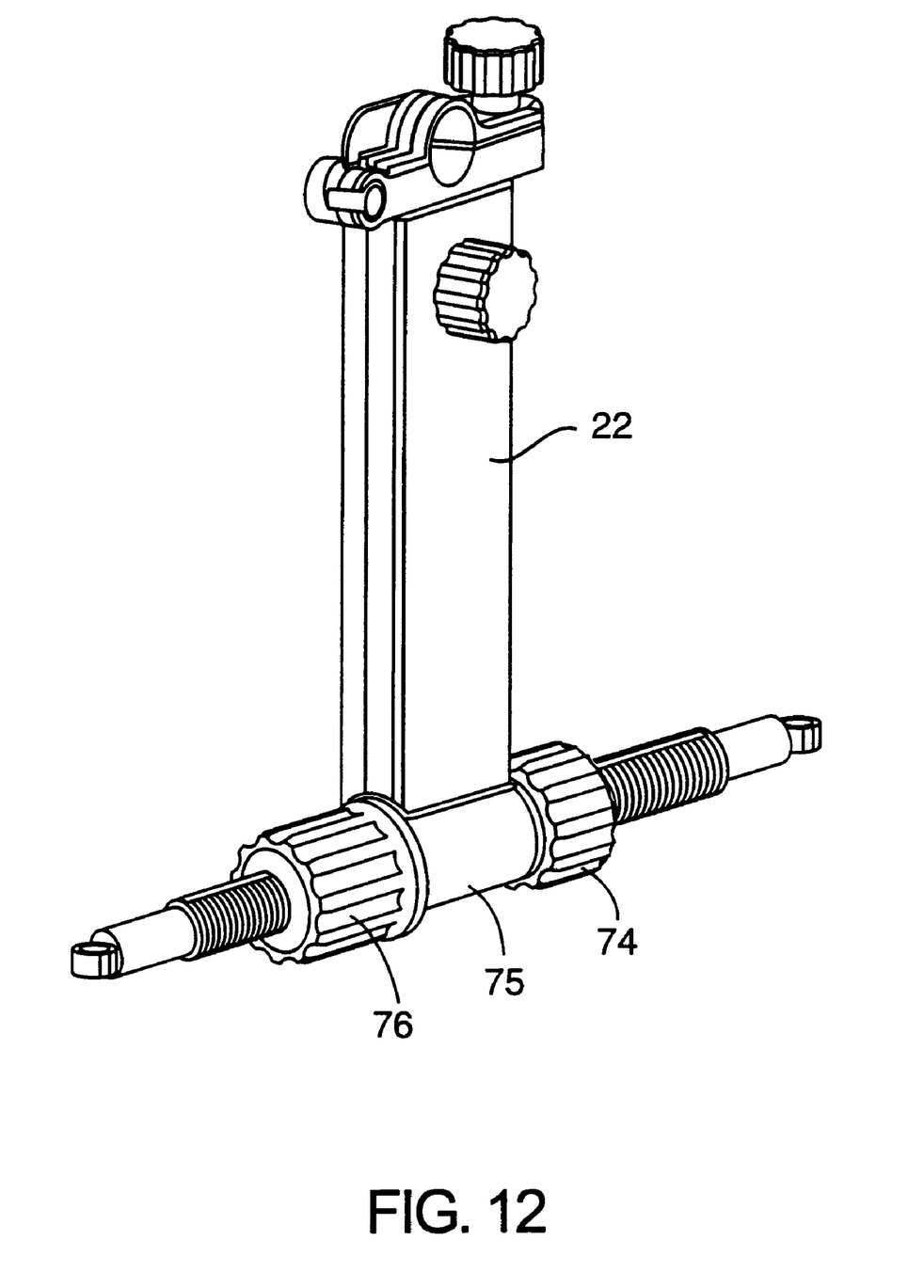
FIG. 12 is an side perspective view of the mechanism connecting an upward support to a guide rail.

As described above, and as seen in FIG. 3, cannula guide 28 is adapted to rotate in direction R2 about axis 34. Similarly, cannula guide 26 is adapted to rotate in direction R2 about axis 32. In another aspect of the invention, cannula guides 26 and 28 are adapted to rotate such that a cannula received therein can be rotated about a point at or near its distal end. Specifically, as illustrated for cannula guide 26 in FIGS. 9 and 11, a curved groove G can be provided attaching cannula guide 26 to cannula holder 40 such that cannula holder 40, (and cannula 55 therein), is rotatable in direction R5 about point 70 while a cannula guide 26 is rotatable about axis 32, thus enabling cannula 55 to be angled slightly such that it rotates about a point (70) proximal its distal end. Movement of cannula 55 in direction R5 facilitates the selection of various angles of surgical intervention, thereby avoiding the potential for injury to structures adjacent the annulus of a patient's intervertebral disc. Moreover, movement of cannula 55 in direction R5 held to avoid contacting various para-spinal nerves when initially approaching intervertebral space 60 with cannula 55.

Figure 10:
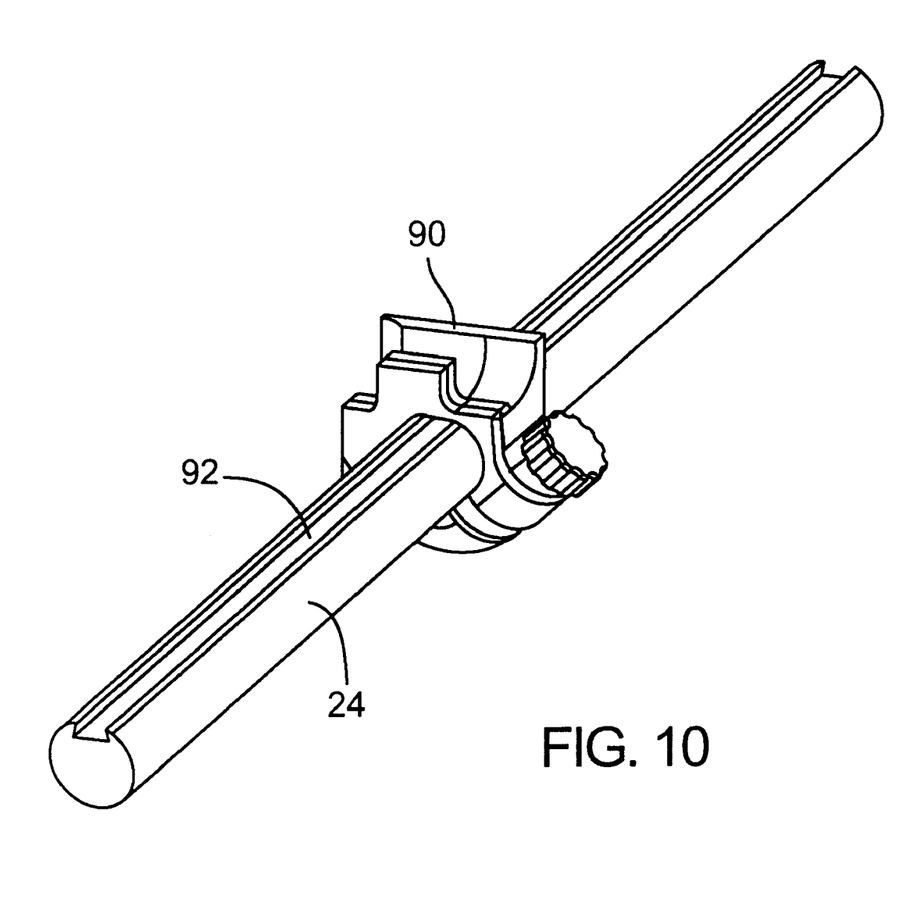
FIG. 10 shows further structural details of a horizontal radio opaque marker and attached mounting system.

FIG. 10 shows a holder 90 for mid-sagittal marker 29. A movable ruler 92 extending from opposite sides of holder 90 has length indicia which assist in positioning cannula holders 26 and 28 at preferred positions along cross member 24.

What is claimed is:

1. A spinal surgery instrument guidance platform, comprising:
    a base;
    a cross member suspended from the base; and
    a pair of cannula guide holders suspended from the cross member,
    a cannula guide suspended from each cannula guide holder, wherein each of the cannula guides remain co-planar with one another both when each of the cannula guides are rotated about an axis perpendicular to a longitudinal axis extending through the cross member and when each of the cannula guide holders are translated in a direction parallel to the longitudinal axis extending through the cross member.

2. The guidance platform of claim 1, wherein, the pair of cannula guides are adjustably positionable at desired positions along a length of the cross member.

3. The guidance platform of claim 1, wherein, the cross member has distance indicia printed therealong.

4. The guidance platform of claim 1, wherein, the pair of cannula guides are adjustably rotatable about the longitudinal axis extending through the cross member.

5. The guidance platform of claim 1, further comprising:
    a pair of elongated radiopaque markers, each marker being adapted to be suspended within one of the pair of cannula guides.

6. The guidance platform of claim 5, wherein, at least one of the radiopaque markers has distance indicia printed thereon.

7. The guidance platform of claim 6, further comprising:
    a surgical instrument received within one of the cannulae.

8. The guidance platform of claim 7, wherein, the surgical instrument is selected from the group consisting of a cannula, bone drill, expandable trocar, nerve surveillance probe, radiopaque marker, intervertebral insert, or intervertebral insert positioning system.

9. The guidance platform of claim 1, further comprising:
    a pair of operating cannulae, each cannula being adapted to be suspended within one of the pair of cannula guides.

10. The guidance platform of claim 9, wherein, the pair of cannula guides are each adapted to rotate cannulae supported therein about a point at or near a distal end of the cannulae.

11. The guidance platform of claim 1, wherein, the pair of cannula guides are each adapted to support a cannula for rotation about an axis extending perpendicular to a central longitudinal axis of the cross member.

12. The guidance platform of claim 1, wherein the base comprises:
   a pair of upwardly extending support members; a pair of guide rails extending in a direction generally perpendicular to the cross member, each of the support members extending upwardly from one of the guide rails.

13. The guidance platform of claim 12, wherein, each upwardly extending support member can be adjustably positioned along a length of one of the guide rails.

14. A method of positioning a cannula along a path in a patient's intervertebral plane, comprising:
   suspending a cross member across a patient, the cross member having two cannula guides attached thereto, the cannula guides each being adjustably movable both along the length of the cross member and around a central longitudinally extending axis of the cross member;
   suspending radiopaque markers from the cannula guides;
   aligning the radiopaque markers with the intervertebral plane as viewed in a radio-image, thereby aligning the cannula guides with the intervertebral plane; and
   advancing a cannula through the cannula guide.

15. The method of guiding a cannula of claim 14, further comprising:
   viewing a radio-image to calculate a vertical distance from the cannula guides to the patient's intervertebral space.

16. The method of claim 15, wherein calculating a vertical distance comprises:
   suspending at least one of the radiopaque markers vertically beside the patient; and
   viewing distance indicia on the at least one radiopaque marker in a radio-image.

17. The method of claim 15, further comprising:
   orienting the cannula in a preferred posterolateral approach.

18. The method of claim 17, wherein, orienting the cannula in a preferred posterolateral approach, comprises:
   positioning the cannula guide at a location on the cross member such that the cannula is oriented in a preferred posterolateral approach.

19. A guidance platform for positioning a cannula along a path in a patient's intervertebral plane, comprising:
   a cross member having two cannula guides attached thereto, the cannula guides each being adjustably movable both along a length of the cross member and around a central longitudinally extending axis of the cross member;
   means for suspending the cross member across a patient;
   means for suspending radiopaque markers from the cannula guides;
   means for aligning the radiopaque markers with the intervertebral plane as viewed in a radio-image, thereby aligning the cannula guides with the intervertebral plane; and
   means for advancing a cannula through the cannula guide.

20. The guidance platform of claim 19, further comprising:
   means for viewing a radio-image to calculate a vertical distance from the cannula guides to the patient's intervertebral space.

21. The guidance platform of claim 20, wherein the radiopaque markers are elongated and have distance indicia printed thereon.

* * * * *